United States Patent [19]

Silvis

[11] 4,322,367
[45] Mar. 30, 1982

[54] DEOILING OF AQUEOUS SOLUTIONS OF SODIUM LAURYL SULFATE

[75] Inventor: Salvatore J. Silvis, Staten Island, N.Y.

[73] Assignee: Colgate-Palmolive Company, New York, N.Y.

[21] Appl. No.: 97,520

[22] Filed: Nov. 26, 1979

[51] Int. Cl.$^3$ .............................................. C07C 141/04
[52] U.S. Cl. ................................................. 260/459 R
[58] Field of Search ..................................... 260/459 R

[56] References Cited

U.S. PATENT DOCUMENTS 3,865,861   2/1975   Sowerby ......................... 260/459 R

*Primary Examiner*—Alan Siegel
*Attorney, Agent, or Firm*—Richard N. Miller; Murray M. Grill; Herbert S. Sylvester

[57] ABSTRACT

Free oil, often an objectionable impurity in synthetic organic detergents, such as sodium lauryl sulfate, is removed from aqueous solutions by extraction thereof with hexane in the presence of lower alkanol, with the proportion of the alkanol present being in a relatively narrow range with respect to the sodium lauryl sulfate, in which range it helps to promote efficient extraction of the free oil by the hexane without solubilizing the hexane in the aqueous medium to such an extent as to result in an extracted detergent containing an unacceptably high proportion of hexane. Separation of the free oil from the aqueous detergent solution is effected in an extractor, to which the hexane is added, in mixture with a minor proportion of lower alkanol, normally isopropanol, and extraction of the free oil takes place after a preliminary mixing of isopropanol with detergent acid or neutralized base in a neutralization vessel and/or in a mixer upstream of the extractor. In a preferred embodiment of the invention the hexane extractant feed to the extractor is that resulting from distillation separation from the free oil of the hexane with some isopropanol. Also, extracted product is evaporated and the evaporator overhead, including isopropanol, hexane and water, is fed to the mixer. The evaporator product is steam stripped, very preferably in a novel stripper described herein, and the stripper overhead, including isopropanol and water, is conveniently fed to a neutralization vessel in which detergent acid, comprising the product of sulfation of lauryl alcohol with sulfur trioxide (and containing objectionable free oil), is neutralized with aqueous sodium hydroxide. Preferably the deoiling process is a continuous one, with only free oil being removed from the extractor feed, and the hexane and isopropanol are continuously recycled.

17 Claims, 2 Drawing Figures

Fig. 1

DEOILING OF AQUEOUS SOLUTIONS OF SODIUM LAURYL SULFATE

This invention relates to the deoiling of synthetic detergents. More particularly, it relates to removal by extraction of undesirable free oil present in aqueous solutions of synthetic organic detergents, particularly when the detergent is sodium lauryl sulfate and when the free oil is that resulting from sulfation of lauryl alcohol with sulfur trioxide, followed by neutralization with sodium hydroxide. However, the invented process may also be applied to removing free oil from other detergent solutions.

Free oil, which usually includes unreacted, partially reacted or decomposed lipophilic reactant that is employed in the manufacture of a synthetic organic detergent, as well as lipophilic impurities and contaminants, is usually an objectionable component of such a detergent product and therefore, it is often preferred that it be removed. Usually the free oil or "ether soluble component" has no desirable detersive properties, often lowers detergency, interferes with foaming of the product, adversely affects color, odor and taste, and is generally considered to be objectionable in the finished product. Accordingly, it has usually been specified that the free oil content of a synthetic organic detergent should be low, being below 1.0 or 1.5% of the detergent, preferably less than 0.5% thereof and often less than 0.4% thereof, by weight. Although the free oil may be insoluble in water, it is generally emulsifiable or can be solubilized in small quantities, in aqueous detergent solutions. Frequently, it may be solubilized by polar solvents, e.g., lower alcohols, which may be present in the product solution. Hence, it is often difficult to remove free oil from such solutions. Free oil may be extracted from solid synthetic organic detergents by a suitable lipophilic extractant or solvent but it is often more economical to be able to avoid using any special drying process, while making the product from usual aqueous solutions of detergent salt, resulting from neutralization of a detergent acid. Yet, when it is attempted to use such lipophilic solvents or extractants to extract aqueous solutions of anionic synthetic organic detergent salts, interfering emulsions and gels may be formed. Having materials present in the solution to be extracted which aid in preventing such emulsification and/or gelation can result in contamination of the detergent and/or solvent with such materials. If a polar solvent is used to inhibit emulsification and gelation there can result a cosolvent effect so that objectionable amounts and proportions of free oil and lipophilic solvent or extractant are contained in the aqueous detergent-containing medium after extraction. In some cases hexane can even be solubilized in the detergent layer. Also, the employment of extractants often gives rise to recovery and disposal problems, especially with respect to solvent recovery.

The present invention is of a method of deoiling a synthetic organic detergent salt, in particular, an anionic detergent, and more particularly, sodium lauryl sulfate, by treatment of an aqueous solution of such salt, containing free oil, with a lipophilic extractant, such as hexane, in such manner as to result in the production of an aqueous solution of such detergent salt, preferably containing less than 0.5% of free oil on a detergent weight basis. In accordance with the present invention a method for deoiling an aqueous solution of sodium lauryl sulfate comprises bringing into contact a liquid phase comprising sodium lauryl sulfate to be deoiled, oil to be removed therefrom, water, isopropanol and hexane, with the proportion of isopropanol: sodium lauryl sulfate being within the range of 1.3 to 2.5, by weight, and a liquid phase comprising hexane and isopropanol, separating the liquid phases into upper and lower parts, with hexane, isopropanol, free oil and a small amount of water in the upper part and sodium lauryl sulfate, isopropanol, water and hexane in the lower part, separating hexane and isopropanol from the free oil of the upper part material, preferably evaporating lower material to remove portions of the isopropanol, hexane and water therefrom and to increase the concentration of the sodium lauryl sulfate in the aqueous solution thereof, and stripping alcohol from the lower or evaporated solution resulting. The minor amount or proportion of water in the extractor upper part may be a negligible amount or proportion. It may remain with the free oil residue from the hexane vaporizer or it can go off with the hexane, depending on the vaporizing conditions. Preferably, the deoiling process is a continuous one, the extractant and the evaporator and stripper overheads are recycled and only make-up extractant, anti-gelling and anti-emulsification solvent, and water, in certain ranges of proportions of the solvent to detergent, are needed for processing, in addition to the initial reactants for the manufacture of the sodium lauryl sulfate (which are lauryl alcohol, sulfur trioxide and aqueous solution of sodium hydroxide). In the mentioned continuous process the contacting and separation of the liquid phases may take place in a conventional continuous countercurrent extractor wherein premixed feed, containing hexane, is added continuously and the recovered hexane-isopropanol extractant is added continuously. The product layer is withdrawn continuously from the extractor bottom or equivalent location while the extractant is removed from the top or equivalent location. Normally such removals are at bottom and top, respectively, but this may be modified, as in centrifugal separators, etc. Preferably, the invention relates to a continuous process but batch adaptations can be made too. The combination of extraction, evaporation and stripping operations is important to the success of the invention, and the extraction by an extractant that is in substantial equilibrium with the extracted solution (except for the fatty oil) is also important because it permits selective removal of the fatty oil without removals of other solution components, and this makes further processing simpler and more effective.

Prior art patents found in a search conducted in the U.S. Patent and Trademark Office include U.S. Pat. Nos. 2,412,916; 2,441,258; 2,615,833; 2,655,530; 2,673,207; 2,687,420; 3,865,861; 3,941,810; 4,113,438; and 4,113,765, which represent the closest prior art known to the inventor.

U.S. Pat. No. 2,412,916 discloses the purification by extraction of neutralized naphthenic sulfonic acids, wherein the extractant is a light hydrocarbon material (included among which hexane is mentioned). Isopropanol is present in the aqueous medium, which also contains water soluble and water insoluble sulfonates, from which unreacted oil is extracted. U.S. Pat. No. 2,441,258 relates to purification of sulfonic acid salts, such as calcium mahogany sulfonate, by treating such a salt with nitropropane to selectively dissolve mineral oil and other hydrocarbon matter present, allowing the mixture to settle, and separating the layers thereof, after which distillations are employed to recover oil-free sulfonate, nitropropane and hydrocarbon oil. U.S. Pat. No. 2,655,530 teaches the neutralizing of an alkylaryl sulfonic acid in a solvent which includes water, alcohol and hydrocarbon, washing the solution with additional hydrocarbon solvent to remove unsulfonated alkylaryl hydrocarbon material, and then removing the hydrocarbon, alcohol and water to obtain a concentrated aqueous solution of neutralized alkylaryl sulfonate. U.S. Pat. No. 2,673,207 describes the neutralization of acid sulfonation products in a two-phase liquid vehicle containing neutralizing agent. One of the phases is an aqueous phase and the other is an organic solvent phase. Among the organic solvents that are suggested for use are low boiling hydrocarbons. Also, it is mentioned that lower alcohols, such as methyl, ethyl and isopropyl alcohols, are preferred for economic reaons and because of their relatively low boiling points and inhibiting effects on foams. It is also suggested that solvent mixtures may be employed. U.S. Pat. No. 2,687,420 relates to a process for neutralizing sulfonated organic detergent acids in an aqueous organic solvent solution, which separates into two immiscible liquid phases. Among the organic solvents mentioned are isopropanol but water immiscible solvents are also suggested, providing that they become sufficiently soluble in the aqueous medium.

U.S. Pat. No. 3,865,861 teaches the solvent extraction of unreacted alcohol from an aqueous medium containing sulfated and neutralized secondary alcohols, by means of solvent extraction with a water immiscible solvent, such as petroleum ether. The patent teaches that a low boiling alcohol, such as isopropanol, may be present with the neutralized detergent salt being purified. Unreacted alcohol is separated from the detergent salt by such solvent extraction and normally is then freed from the solvent by distillation off of the solvent, after which the alcohol may be recycled for sulfation. The patent also describes stripping off of the solvent alcohol from the detergent salt and recycling of such alcohol to the neutralizer. U.S. Pat. No. 3,941,810 discloses the sulfonation of aromatic compounds by sulfur trioxide in the presence of a suitable solvent, such as hexane, after which the aqueous sulfonate product resulting, in such solvent, is extracted by a mixture of such solvent and an aromatic compound. The aqueous sulfonate resulting, removed from the base of an extraction column, is sent to a stripper, where the final traces of solvent and unreacted aromatic substance are removed from it. The small quantities of water, solvent and unreacted aromatic reactant removed in the stripper are condensed and recycled. U.S. Pat. No. 4,113,438 mentions petroleum ether extraction of free oil from water soluble sulfonate detergents, such as linear alkylbenzene sulfonates and olefin sulfonates. U.S. Pat. No. 4,113,765 describes the use of hexane or other inert solvent with an alkyl aromatic material being sulfonated by $SO_3$. However, the hexane is vaporized off from the sulfonic acid product made before neutralization thereof and is not employed to extract free oil from such detergent acid. The only patent found that is considered to be of any relevance at all to the stripper apparatus, U.S. Pat. No. 2,615,833, shows only the use of steam eductors to lift oily material being stripped and thereby carry it upwardly through a bubble tray column. In addition to the patents found in the search, it is admitted prior art that free oils have been removed from solid neutralized detergents by extraction thereof with ether to determine the percentage of free oil or "ether solubles" present therein.

Although the prior art discloses the purification of aqueous detergent compositions by extraction of free oil therefrom with lipophilic solvents, and although the presence of lower alcohols, such as isopropanol, in detergent solutions being extracted, has been taught, the process of the present invention has not been described nor has it been suggested and it is not obvious from the references nor from any combination thereof. For example, the references do not suggest the importance of the range of proportions of isopropanol:sodium lauryl sulfate, the quick separation of liquid phases in the extractor, the evaporation of the lower phase material and the stripping of the evaporated solution resulting nor, more particularly, do they teach the application of such processes to the purification of sodium lauryl sulfate in a continuous manner and utilizing applicant's novel apparatus, including his stripper.

The invention will be readily understood by reference to the present specification and the accompanying drawing in which.

Figure 1:
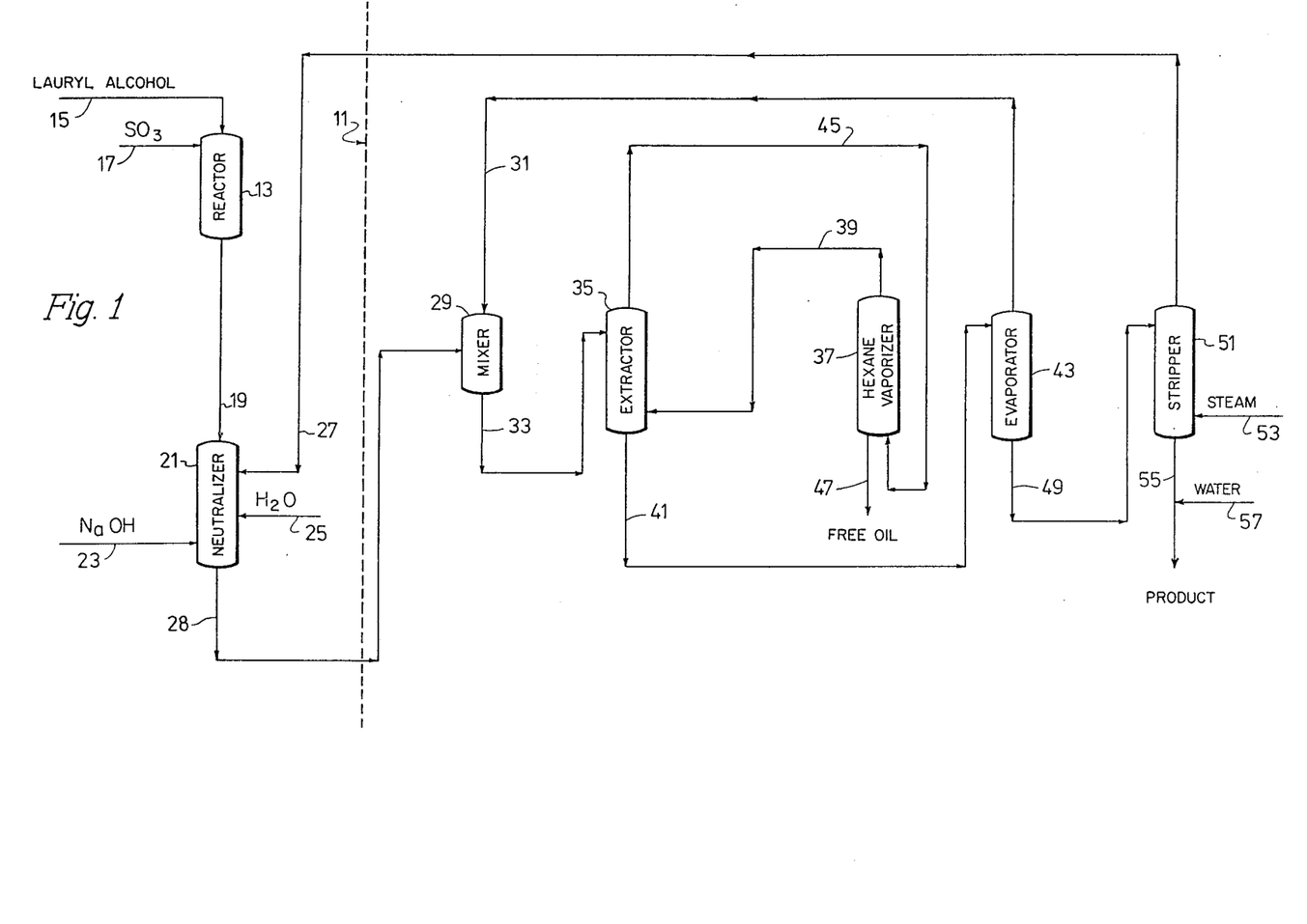
FIG. 1 is a schematic flow diagram illustrating deoiling of a particular detergent, sodium lauryl sulfate, and showing the manufacture of such detergent and the recycling of recovered material to the deoiling amd manufacturing processes.

In FIG. 1 a known method for the manufacture of neutralized detergent containing free oil is shown on the left side of separating line 11 and the deoiling of such detergent and the recoveries and recyclings of various materials resulting from the manufacturing and deoiling operations are shown on the right side thereof. Lauryl alcohol and sulfur trioxide gas (which may be pre-blended with diluent gas, such as air or nitrogen) are fed to reactor 13, via lines 15 and 17, respectively, sulfation takes place, and the sulfuric acid ester resulting, unreacted sulfur trioxide present, and free oil are removed from the reactor and are passed via line 19 to neutralizer 21, to which an aqueous solution of sodium hydroxide is added through line 23, water is added via line 25 and recovered stripper overhead, comprising isopropanol and water, is added via line 27. The neutralized base, including sodium lauryl sulfate, free oil, sodium sulfate, isopropanol and water, is passed via line 28 to a mixer 29, in which it is mixed with recovered evaporator overhead, comprising isopropanol, hexane and water, which overhead is fed to the mixer via line 31. The mixture of materials resulting, including sodium lauryl sulfate, free oil, sodium sulfate, isopropanol, hexane and water, is fed through line 33 to extractor 35, to which recovered hexane, with isopropanol, is fed from hexane vaporizer 37 through line 39. In the extractor the feed mixture and recovered hexane extractant material are brought into intimate contact with each other, the feed, for the most part falling, and the extractant rising, so that the fatty oil is extracted by the upwardly moving extractant liquid. The lower, hydrophilic layer of extracted product resulting, including sodium lauryl sulfate, a minor proportion of the free oil charged to the extractor, sodium sulfate, isopropanol, hexane and water, is removed via line 41 and is fed to evaporator 43, and the upper lipophilic layer, comprising hexane, isopropanol and a major proportion of the free oil that had been charged to the extractor (often plus a small, sometimes negligible proportion or amount of water), is removed and sent through line 45 to the hexane vaporizer. From such vaporizer (or hexane recovery unit), which is maintained at an elevated temperature, e.g., 65°–85° C., hexane and isopropanol are removed overhead and condensed, and subsequently pass through line 39 to the extractor, and the free oil is taken off through line 47. The free oil may be recycled back to reactor 13 with the lauryl alcohol reactant charged, if desired, but such recycling is not normally practiced because of the usual objectionably dark color of the free oil and its variable content of lauryl alcohol. From evaporator 43, which is a wiped-film type of evaporator to prevent poor heat transfer to the solution being evaporated due to gel formation at higher detergent concentrations thereof, and which operates under vacuum, the mixture of isopropanol, hexane and water previously mentioned is taken off and sent to mixer 29 through line 31, while the evaporator product, comprising sodium lauryl sulfate, a small proportion of free oil, sodium sulfate, isopropanol, and water, is removed through line 49 and is fed to stripper 51, which is operated under vacuum and at a temperature which may be slightly higher than that of the evaporator. The evaporator is of the wiped-film type because otherwise the hea transfer surface will become blocked with gel and will be inactive, which can cause degradation of the detergent and inoperativeness of the evaporator. Usually the evaporation product contains practically no hexane, but a small proportion, e.g., 0.1 to 0.3%, may be present. Steam is admitted to stripper 51 through line 53 aand the overhead from the stripper, isopropanol and water in mixture, is sent to neutralizer 21 through line 27, as previously described. The product, comprising sodium lauryl sulfate, a very small percentage of remaining free oil, sodium sulfate and water, is removed through line 55. Additional water, for final concentration control, mixes with the product in line 55, being fed to such line through line 57.

Figure 2:
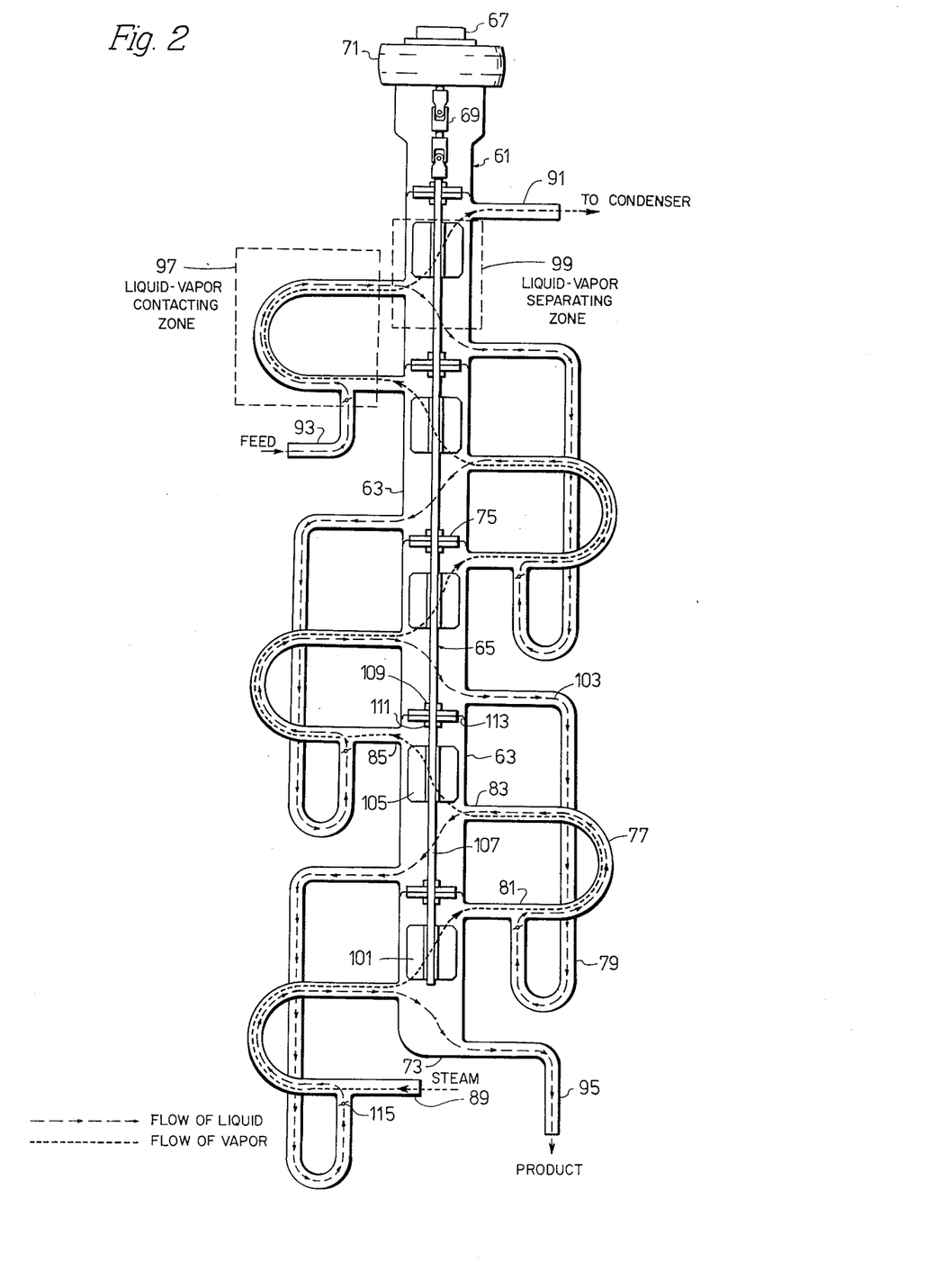
FIG. 2 is a partially centrally sectioned elevation of a novel stripping column for use in the described deoiling process, for removal of alcohol (and water) from the deoiled detergent solution.

In FIG. 2 is shown the construction of a novel stripping column for use in the process of the present invention to separate lower alkanol (isopropanol) from synthetic detergent (sodium lauryl sulfate), inorganic salt (sodium sulfate), water and the small proportion of unextracted free oil remaining. The present stripper, which may be utilized for other separations, too, is especially advantageous in the process of this invention because it separates solvent from aqueous detergent solution without the virtually insurmountable foaming problems which are otherwise often encountered in making such separations. This column is unique in that it permits foaming solutions to be rectified in a continuous, countercurrent manner, which up to now has been impossible.

Numeral 61 represents the stripping column, which comprises a cylindrical wall portion 63, internal agitation (foam-breaking) means 65 (which is not always required), drive means 67, connecting means 69, between the drive and agitation means, upper sealing means 71, lower sealing means 73, separators 75, for separating the column into sections, vapor-liquid contacting lines 77, liquid lines 79, vapor-liquid mixing means 81, entrances 83 for additions of vapor-liquid mixtures to the column, exits 85 for vapor leaving the column, exits 87 for liquid leaving the column, steam or stripping gas inlet 89, vapor outlet 91, feed inlet 93 and product outlet 95. Numeral 97 designates what may be characterized as a liquid-vapor contacting zone and a liquid-vapor separating zone is represented by numeral 99. Paths of vapor and liquid are designated respectively by numerals 101 and 103.

In column 61, which may be of a single piece, with inlets and outlets provided thereon, or may be of a plurality of component parts, fastened together, liquid-vapor separating elements 105 can be provided in each column section, if deemed desirable, as a part of unified agitator 65, between column separating members 75. As illustrated, liquid-vapor separating members 105 are paddles, shown as of blade form, affixed to rotatable shaft 107, which shaft is mounted in bearings 109 and 111. As shown in the drawing, such bearings are associated with column separators 75, which include sealing gaskets 113 around the peripheral portions thereof.

In the mixing portion of the apparatus, wherein steam or vapor mixture is brought into intimate contact with liquid from which lower alkanol, e.g., isopropanol, is being separated by vaporization, such contact may be effected due to the Venturi nature of the mixing tee 81, not illustrated, and in the connecting piping 77, which, to obtain better mixing effects, may be at last partially packed with any of various suitable types of packing, e.g., corrugated metal strips. To prevent unintentional back-feeding of liquid, which might possibly occur due to momentary steam pressure increases, check valves, such as that illustrated at 115, will preferably be installed, thereby preventing back-feeding of the liquid and bypassing by it of the vapor. In the illustration the U-tube shaped legs of the side passages help to prevent "blow-by" of steam of vapor but the use of check valves is more positive and is of further assistance. At the column bottom a U-shaped line or equivalent means is provided, not shown, to maintain liquid in the column or drain line 95, so as to prevent steam or vapor escape through that line.

In operation, the present stripping apparatus, normally covered with insulating material (not shown) around the various parts thereof so as to minimize heat losses, is fed at 89 with steam at the desired temperature, pressure and rate, which steam (and later, steam-isopropanol mixture) passes through outlet 91 to a condenser, not shown, and addition of the feed, comprising detergent, inorganic salt, lower alkanol, water and a small proportion of free oil, is commenced through inlet 93. The path of the vapors up the column is apparent from the drawing and it is seen that vapor will mix with the feed in the mixing or Venturi tees and will carry the liquid feed upwardly through the side pipings back into the column, where paddles or beaters 105 will help to separate any foam resulting into liquid and vapor phases. (It will be evident that the numerals for the various parts of the invention relate to each of the replications of such parts in the column). Then, a vapor, enriched in isopropanol as a result of the mass transfer occurring in the liquid-vapor contacting zone, will pass out exit 91 to the condenser, for condensation to liquid. Also the liquid, from which some isopropanol has been removed, will travel downwardly through line 79 until it fills the U-shaped portion thereof. Again, but this time in a lower portion of the column, the mixture of liquid and vapor will be separated into liquid and vapor phases, the vapor will move upwardly and the liquid will move downwardly, and the operations will be repeated. In each stage as the liquid moves downwardly through the column, it has isopropanol removed from it by a vapor which is leaner in its equilibrium isopropanol content as the bottom of the column is approached. Correspondingly, as the feed descends through the column it will lose isopropanol, so that when it is withdrawn from the stripper the isopropanol content will be essentially nil.

The materials of construction of the stripping column will preferably be non-corrosive, such as stainless steel, glass or plastic, e.g., fiberglass reinforced polyester resin. However, other suitable materials may also be employed, including ceramics, steels, aluminum, other metals and alloys, phenol-formaldehyde resins, nylons, polypropylene, polyethylene, neoprene, polyurethane, polytetrafluoroethylene, etc., depending on the function to be performed by a particular part. So as to provide for visual observation of the effectiveness of the foam-breaking or agitating means, sight glasses may be provided in the column wall. Instead of using paddles or beaters for breaking foam, other means may be employed, including centrifugal or cyclone separators, internally located (within the stripping column) or externally positioned. The piping, illustrated externally of the column in FIG. 2, may be relocated internally thereof and such relocation is especially convenient and practicable when internal centrifugal separators or equivalent devices are employed to break the foam.

An important feature of the present invention is that the steam or vapor will be brought into intimate contact with the liquid from which a volatile component is being vaporized and removed, and that after being brought into such intimate contact the vapor and liquid are separated, with the vapor continuing to pass onwardly (upwardly) into a series of other contact and separation areas, whereas the liquid passes in an opposite direction (downwardly), after separation from the entraining vapor, to where it is contacted by upwardly moving vapor and subsequently is directed to a lower (than the previous) separating zone, from which it then continues to move downwardly. The upward movement of vapor and the downward movement of liquid being stripped superficially resemble conventional distillation and stripping column operations, with respect to component movements, but because such apparatuses usually employ bubble caps or other means for providing liquid levels on plates and for bringing liquids and gases into contact, they often create objectionable foaming and additionally, are often not as efficient in bringing the contacting liquid and vapor phases into equilibrium in the short contact periods of the column operations. The present apparatus overcomes these difficulties and disadvantages. In this apparatus, for example, vapor speeds of about 10 to 200 meters/second, preferably 20 to 150 m./sec., e.g., 30 m./sec., are practicable, with good efficiencies in reaching equilibrium between liquid and vapor, and efficient separation of the liquid and vapor. In the event that the separation is not adequate with five column sections, such as illustrated, the number thereof may be increased and it is contemplated that as many as a hundred such sections can be employed, although normally the number thereof will be from 3 to 30, preferably being from 4 to 20. Of course, column size may be adjusted, as desired, but normally the column diameter will be from 0.1 to 3 m., preferably 0.2 to 1.5 m. and the column section length will be from 0.1 to 1 m., preferably from 0.1 to 0.5 m. The column cross-sectional shape will preferably be circular but other shapes, e.g., square, rectangular, hexagonal and elliptical, may be used, and may be particularly advantageous to provide room for internal mixers, separators and passageways.

The detergent material being purified by the method of this invention, as described herein, is very preferably sodium lauryl sulfate in an aqueous medium containing water and free oil. Other materials may be present with the active detersive ingredient (A.I.), such as sodium sulfate and polar solvent, such as lower alcohol, e.g., isopropanol. Such aqueous solutions will normally contain from 25 to 33%, preferably from 28 to 32% and most preferably 30 to 32% of sodium lauryl sulfate; 1.0 to 6% usually 1.0 to 4% and frequently 1.2 to 3% of free oil, 0.3 to 3%, usually 0.4 to 2.5% and frequently 0.5 to 2% of sodium sulfate; 0 to 10%, usually 0.1 to 8% and often 1 to 5% of lower alkanol, e.g., isopropanol; and 50 to 75%, usually 55 to 70% and typically 60 to 67% of water. On a detergent A.I. basis the ranges of proportions are 3.2 to 19.4, 3.2 to 12.9 and 3.9 to 9.7 percent or parts per hundred for the free oil; 1 to 9.7, 1.3 to 8.1 and 1.6 to 6.5 for the sodium sulfate; and 0 to 32.2, 0.3 to 25.8 and 3.2 to 16.1 for the lower alkanol. The neutralized base may also contain other materials normally present in detergent compositions but preferably the contents thereof will be minimized, normally being limited to 10%, preferably 5% and most preferably 1%, on dry basis. Of course, when other detergents are being deoiled their initial and final oil contents may differ from those given above, and even with the higher alcohol sulfates being purified, oil contents outside the ranges given may be encountered and may result.

Although the neutralized base to be deoiled may best be made with a low content of inorganic salt and free oil by sulfation of lauryl alcohol with gaseous sulfur trioxide and subsequent neutralization in an aqueous medium with aqueous sodium hydroxide solution (often of 5 to 15% NaOH content therein), and often in the presence of a desired quantity, such as that previously described, of isopropanol or other suitable lower molecular weight polar solvent (which may help to prevent gelling and excess foaming), other manufacturing methods may also be utilized which result in comparable aqueous solutions or similar aqueous media of such concentrations of components as were mentioned previously. Thus, a neutralized base product of oleum or sulfuric acid sulfation of lauryl alcohol may also be employed. Furthermore, although the proportions of various components of the neutralized base and extractant materials, and the conditions of the present invention, are important with respect to the manufacture of desired deoiled sodium lauryl sulfate product, such concentrations, proportions and conditions, sometimes with minor variations, may also be useful in the manufacture of corresponding higher fatty alcohol sulfates, such as those wherein the higher fatty alcohol sulfate is of 10 to 18 carbon atoms, e.g., 12 to 16 carbon atoms, or is a mixture of alcohols of such type, e.g., those obtained from coconut oil and other nut, seed or kernel sources. Also, the deoiling method described may be successfully applied to removing unwanted free oil from other synthetic organic detergents, but is especially useful for purifying the anionic detergents, such as higher fatty monoglyceride sulfates and sulfonates, higher fatty alcohol polyethoxy sulfates, linear higher alkylbenzene sulfonates, alkyl sulfonates, olefin sulfonates and paraffin sulfonates. With respect to such detergents and the preferred fatty alcohol sulfates, while the sodium salts thereof are normally utilized, other salts may also be purified by the method of this invention, including those of other alkali metals, such as potassium, water soluble salts of alkaline earth metals and magnesium, ammonium salts and alkanolamine salts, such as triethanolamine salts. Usually the anionic detergents will include a linear alkyl of 8 to 20 carbon atoms, preferably a higher alkyl of 12 to 18 carbon atoms. For example, the following detergents may also be deoiled by methods substantially like those described herein for the preferred sodium lauryl sulfate: sodium linear dodecyl benzene sulfonate; sodium linear tridecyl benzene sulfonate; sodium hydrogenated coconut oil fatty acids monoglyceride sulfate; sodium lauryl monoglyceride sulfonate; sodium ethoxylated lauryl alcohol sulfate (3 mols ethylene oxide per mol); sodium ethoxylated lauryl alcohol sulfate (2 mols ethylene oxide per mol); sodium alpha-olefin sulfonate (12-18 carbon atom content olefin); sodium alpha-olefin sulfonate (12-14 carbon atom content olefin); sodium alpha-olefin sulfonate (16-18 carbon atom content olefin); and secondary higher alcohol sulfates.

The lipophilic solvent, while preferably hexane, may also be other alkanes, e.g., pentane, heptane and mixtures of such materials, usually preferably being linear alkanes of 4 to 9 carbon atoms, but other hydrocarbons and equivalent lipophilic solvents may also be employed. Desirably, such materials will have normal boiling points in the range of 50° to 75° C., preferably 65° to 70° C. However, by adjustment of distillation, evaporation, stripping and extraction conditions, one may employ other solvents, having other boiling points and ranges, and may utilize appropriate mixtures thereof.

The polar solvent employed is very preferably isopropanol but other lower alkanols, such as methanol and ethanol, may also be used, as may be equivalent hydrophilic solvent materials capable of inhibiting emulsification and/or gelation of the detergent and the lipophilic solvent under the processing conditions employed. Hereafter, for simplicity, reference will be to the prevention of gelation but it is to be understood that such reference is meant to relate to prevention of emulsification, too, with gelation prevention and without. The water used will preferably be deionized water, to avoid any interfering reactions of impurities in the water with the detergent and other materials which may be present, but ordinary tap water may also be used, depending largely upon the purity of the final product desired.

By following the method of this invention there may be produced an aqueous solution of the desired detergent salt wherein the free oil content has been reduced to less than 1%, preferably less than 0.5% and more preferably, less than 0.4%, e.g., to 0.3% or less, on a detergent A.I. basis, and in some cases the final free oil content may be almost nil. Such is often important in producing satisfactory products incorporating the particular detergent. Thus, the presence of free oil may otherwise have a destabilizing effect on perfumes and colors of products, can inhibit foaming, can make products undesirably pasty and, in liquid products, can cause separation of oily layers from the products. When synthetic organic detergents other than sodium higher fatty alcohol sulfate are purified of free oil, which oil usually contaminates such detergents as a result of manufacturing processes, corresponding diminutions of oil contents are also obtainable and are advantageous. On an A.I. (active ingredient or detergent solids) basis, the sodium sulfate content of the deoiled product will usually be in the range of 0.5 to 5%, often being from 1 to 3% and typically being from 1 to 2%. The A.I. concentration in the aqueous solution of product will usually be from 25 to 35%, preferably 27 to 33%, and typically 28.5 to 31.5%, e.g., 30%, but it can vary, too. Normally, it will be a concentration at which gel is not formed.

In practicing the method, the neutralized base, containing free oil, is charged to a mixer, wherein it is mixed with the recovered hexane, isopropanol and water from the evaporation stage at a suitable temperature, usually in the range of about 15° to 70° C. preferably from 30° to 55° C., more preferably 35° to 45° C. and most preferably about 40° C., at atmospheric pressure (or 0.9 to 1.1 atmosphere) for a time long enough to result in intimate mixing of the base and the solvent mix, so that a single phase results. Such mixing time, is not critical, but is usually in the 1 to 10 minute range.

The extractor will normally be operated at the mentioned temperatures and at a pressure of 0.9 to 1.1 atmosphere, preferably at atmospheric pressure. The feeds to the extractor will be within the temperature ranges described for the mixer, which, in some instances, may involve preliminary temperature adjustments of feed components. In continuous extraction, all that is needed is for the contact time between the two phases in the extractor to be sufficient for adequate transfer of the free oil from the detergent solution to the extractant. Such time will usually be within the 1 to 10 minute range but more or less time for holdup in the extractor may be taken. In the extraction the feed may be in dispersed form at the top and drops of it may fall through the extractor, intimately contacting the solvent phase but without any of the feed except the free oil dissolving in it. In other words, the two liquid phases remain immiscible so the hexane and alcohol do not transfer between the phases but the phases are in close contact in the extractor so that the free oil can and does pass to the hexane-isopropanol phase. While continuous operations are highly preferred the operations may be carried out batchwise, too.

The upper liquid phase removed from the extractor will usually comprise from 85 to 99%, preferably 90 to 96% of hexane, 2 to 15%, preferably 4 to 8% of isopropanol, and the maximum free oil content compatible with producing the desired deoiled product. Often such oil content can be 0.1 to 1%, preferably 0.2 to 0.5%. Water content, if any, can be 0 to 1%, preferably 0 to 0.2%. The product removed from the base of the extractor, which usually will weigh from 35 to 65%, preferably 45 to 55% of the weight of the upper body discharged from the extractor, will usually comprise from 10 to 20% of A.I., preferably 14 to 18% thereof, 0.0 to 0.2% of free oil, preferably 0.02 to 0.1% thereof, 0.0 to 0.5% of $Na_2SO_4$, preferably 0.1 to 0.3% thereof, 15 to 40% of isopropanol, preferably 20 to 30% thereof, 5 to 25% of hexane, preferably 10 to 20% thereof, and 30 to 50% of water, preferably 40 to 45% thereof. Within the ranges given it is considered important for best results that the ratio of isopropanol:A.I. in the detergent solution to be deoiled should be in the range of about 1.3 to 2.5, preferably 1.3 to 2, e.g., about 1.5. Such will also be the ratio of these components in the extracted product when the process is operating at peak performance.

The upper lipophilic phase from the extractor is passed in its entirety to a hexane vaporizer operating at atmospheric pressure (or at a pressure in the 0.9 to 1.1 atmosphere range, although greater vacuums are sometimes desirable, e.g., to 0.1 or 0.2 atmosphere absolute), and at a temperature in the range of 65° to 90° C., preferably 70° to 80° C., e.g., 75° C., and the free oil is separated from the hexane and isopropanol charged, with the free oil being removed almost completely or completely from the bottom of the vaporizer and with the hexane, isopropanol and a small amount of water (in some cases) being removed from the top thereof. The hexane-alcohol mix removed is of a very high purity, containing less than 0.1% of free oil, on a weight basis, preferably less than 0.05% of free oil and most preferably 0.04% or less of such oil. Holdup time in the hexane vaporizer will usually be from 0.1 to 30 minutes, preferably 0.5 to 10 minutes and more preferably, about 1 to 5 minutes.

The deoiled extractor product is passed into an evaporator of the wiped-film type, wherein the material to be evaporated passes through a narrow, preferably peripheral, passageway in contact or operative relationship with heat transfer means. To prevent any buildup of gel or other deposit in such passageway or on such heat transfer means the surfaces thereof are continually wiped by passing wiping means over them (and often in contact with them). In the evaporator the temperature will usually be in the range of 25° to 100° C., preferably 60° to 75° C., but the temperature used depends upon the stability of the detergent being processed. The pressure will usually be in the range of 150 to 350 torr, preferably 200 to 300 torr. Holdup time in the evaporator will generally be from 0.01 to 20 minutes, preferably 0.02 to 1 minute and more preferably 0.02 to 0.2 minute. The evaporator overhead removed will normally include from 40 to 60% of isopropanol, 20 to 40% of hexane and 10 to 30% of water, with such proportions preferably being 45 to 55% of isopropanol, 25 to 35% of hexane and 15 to 25% of water. The evaporator product removed may contain from 25 to 40% of A.I., preferably 27 to 37% and more preferably 30 to 34% thereof, and the percentage of free oil will be from 0.0 to 0.5%, preferably being from 0.0 to 0.3% and more preferably from 0.0 to 0.2%, e.g., 0.1%. Isopropanol content will normally be from 1 to 10%, preferably 1 to 5% and more preferably 2 to 4%, and hexane content will usually be in the range of 0.0 to 0.5%, preferably 0.0 to 0.2% and more preferably 0.0 to 0.1%. The water present will usually be from 50 to 80%, preferably 60 to 70% and more preferably 62 to 66%. The proportion of evaporator overhead to evaporator product taken off will normally be from 0.7 to 1.5, preferably 0.9 to 1.2, more preferably 0.9 to 1.1, e.g., about 1. These figures, and others given above, are for sodium lauryl sulfate purification from free oil and can vary when other detergents are processed.

In the stripper the temperature and pressure will be held about the same as those in the evaporator, from which the evaporator product is fed to the stripper, but the stripper temperature may be slightly higher, e.g., 1°–10° C. or 2°–5° C. higher. For stripping, the only material charged to the stripper, in addition to the charge to be stripped, is steam, and the proportion thereof is about 15 to 30% of the total weight of water charged to the stripper in the solution to be purified, preferably being 20 to 25% thereof. Usually one weight of steam is enough to vaporize three weights of lower alkanol, so if allowances are made for heat losses in the equipment, and if one knows the alkanol content of the solution to be stripped, the minimum steam charge can be calculated easily. However, usually an excess is employed, with the proportion of steam charged to isopropanol to be removed being in the range of about 4:1 to 10:1, preferably 4:1 to 6:1, e.g., 5:1. The stripper overhead comprises from 10 to 30% of isopropanol and 90 to 70% of water, preferably 15 to 30% and 85 to 70%, respectively. To the stripped product removed there is added additional water for accurate control of final product composition, with the proportion of water in such product being 60 to 80%, preferably 65 to 75%, the proportion of A.I. being 20 to 40%, preferably 25 to 35%, the proportion of sodium sulfate being 0 to 10%, preferably 0 to 1% and the proportion of free oil being from 0 to 0.2%, preferably 0 to 0.1%. Such concentration will be chosen to avoid gelation.

Of course, while the described operation proportions are preferred, they may be varied, providing that the process effected is essentially the same. Also, some variations may be made between "batch" and continuous processes and when different detergents are being deoiled. However, it is important to utilize only enough of the anti-emulsification and anti-gelling agent (isopropanol, in a preferred case) as needed, so as to prevent any excess amount thereof from helping to solubilize the lipophilic solvent and the lipophilic free oil, which would make deoiling of the detergent more difficult. Variations may also be made in the processing conditions, e.g., temperatures, pressures, times, mixing techniques, while still operating within the invented method.

The following example illustrates but does not limit the invention. Unless otherwise indicated, all parts are by weight and all temperatures are in degrees Centigrade throughout this specification.

EXAMPLE

A neutralized detergent base, consisting of 31.6% of sodium lauryl sulfate (A.I.), 1.3% of free oil (higher fatty alcohol, etc.), 0.5% of $Na_2SO_4$, 3.4% of isopropanol and 63.2% of water, is made by reacting 525 parts of lauryl alcohol and 207 parts of sulfur trioxide in a reactor, according to a known method, to produce 695 parts of the desired sulfuric acid ester, 30 parts of free oil and 7 parts of sulfur trioxide, and then neutralizing such acid mix with 1,639.4 parts of dilute sodium hydroxide solution, containing 107 parts of sodium hydroxide, 1,452.4 parts of water and 80 parts of isopropanol. 320 Parts of the water and the isopropanol came from stripper overhead, which was returned to the neutralizer. During the neutralization reactions 12 parts of sodium sulfate are formed, plus 46.7 parts of water. Thus, the neutralized base mixture removed from the neutralizer contains 750 parts of sodium lauryl sulfate, 30 parts of free oil, 12 parts of sodium sulfate, 80 parts of isopropanol and 1,499 parts of water, making a total of 2,371 parts.

The 2,371 parts of base mixture, the free oil content of which is to be diminished so as to make the product satisfactory for use as detergent component of a dental cream product, are added, at a temperature of 45° C. to a mixer, to which evaporator overhead consisting of 1,070 parts of isopropanol, 690 parts of hexane and 496 parts of water, is added, and mixing is commenced and continued for about five minutes. After thorough mixing of the neutralized base and evaporator overhead, so that a single phase is produced, 4,627 parts thereof are continuously added at about 40° C. to an upper portion of a conventional extractor, and 9,000 parts of a recovered hexane-isopropanol mixture (94% hexane and 6% isopropanol), including 8,460 parts of hexane and 540 parts of isopropanol, are added at 40° C. to the extractor at a lower portion. The extractor is maintained at about atmospheric pressure and the lighter solvent phase, immiscible with the aqueous phase, rises through the extractor as a continuous phase and is withdrawn at an upper portion thereof, while the heavier, aqueous phase, initially converted to droplet form, falls through the extractor and is removed at the bottom thereof as a continuous phase, essentially free of oil. The solvent phase removed at the top of the extractor contains 8,460 parts of hexane, 540 parts of isopropanol and 27 parts of free oil. This mixture, at 40° C., is fed to a hexane vaporizer, at atmospheric pressure and at a temperature of 80° C., and a 94% hexane content hexane-isopropanol distillate is removed at the top of the vaporizer (a negligble proportion of water may also be present), is cooled and is returned to the extractor, as previously mentioned. 27 Parts of free oil are removed from the bottom of the vaporizer. Although such free oil may be recycled, usually it is disposed of as waste, largely because of its objectionable color and odor, which make it an undesirable component for many products and an undesirable reactant to produce products intended for ingestion or personal use.

The extractor product, from which a significant proportion of free oil has been removed, which product includes 750 parts of A.I., 3 parts of free oil, 12 parts of sodium sulfate, 1,150 parts of isopropanol, 690 parts of hexane and 1,995 parts of water, making a total of 4,600 parts, is next subjected to evaporation to remove solvents therefrom and to concentrate it. In the wiped film evaporator used, operated at a temperature of 60° C. and a pressure of 250 torr, with a residence time of about two seconds, 4,600 parts of extractor product are reduced to 2,344 parts of evaporator product, with 2,256 parts of evaporator overhead of the type previously described. The evaporator product consists of 750 parts of A.I., 3 parts of free oil, 12 parts of $Na_2SO_4$, 80 parts of isopropanol and 1,499 parts of water. This evaporator product is subsequently stripped of isopropanol (along with some of its water content) in a stripper of the type illustrated in FIG. 2. The stripper is operated at an absolute pressure of 250 torr and a temperature of 60° to 70° C., with the residence time in the stripper of the evaporator product being about five minutes during its descent from the top to the bottom of the stripper column. In addition to the evaporator product charged, steam is charged to the stripper at the bottom thereof at the rate of about 400 parts per 2,344 parts of evaporator product. At the top of the column the remaining stripping steam and isopropanol vapor with it are condensed and are then returned to the neutralizer, as previously described. At the bottom of the column the product is taken off at a temperature of about 70° C. and about 156 parts of water are blended with it, so as to result in a final product of desired A.I. content, consisting of 750 parts (30%) of A.I., 3 parts (0.1%) of free oil, 12 parts (0.5%) of $Na_2SO_4$, and 1735 parts (69.4%) of water.

During operation of the stripper, if excessive foam is noted in the sight glasses, the paddles operate and break it down, and good separation of isopropanol from the evaporator product charged to the stripper is obtained. The concentrations of A.I. for processing are chosen so as to be below the gelation range thereof, while yet being substantially high. Of course, variations in the proportions of A.I. and water are possible, free oil purifications to different extents may be obtained and other modifications of the method may be made, within this invention.

The deoiling operation described is utilized continuously for several runs over multi-hour periods, and it is considered that on the basis of the experience obtained in these runs, it may be employed indefinitely.

In addition to deoiling sodium lauryl sulfate, the described method may also be employed with other higher alcohol sulfates, including sodium cetyl sulfate, sodium palmityl sulfate and potassium lauryl sulfate. Of course, in these cases and when processing other synthetic organic detergents, temperatures, pressures, proportions, times and other variables will be suitably regulated for best purifications.

In addition to removing free oil from the higher fatty alcohol sulfates, the described process has also been employed to diminish the free oil contents of other anionic detergents in aqueous solution, including: sodium linear dodecyl benzene sulfonate; sodium linear tridecyl benzene sulfonate; sodium hydrogenated coconut oil fatty acids monoglyceride sulfate; sodium ethoxylated lauryl alcohol sulfate (3 mols ethylene oxide per mol); sodium ethoxylated lauryl alcohol sulfate (2 mols ethylene oxide per mol); sodium ethoxylated lauryl alcohol sulfate (1 mol ethylene oxide per mol); sodium alpha-olefin sulfonate (12–18 carbon atom content olefin); sodium alpha-olefin sulfonate (12–14 carbon atom content olefin); and sodium alpha-olefin sulfonate (16–18 carbon atom content olefin). Free oil contents of all were significantly reduced but, because the monoglyceride sulfate was initially considerably higher in free oil content, comparable purification thereof was obtainable with two passes through the extractor.

Although the invention has been described with respect to preferred embodiments and illustrations thereof, various modifications therein may be made without departing from it. For example, instead of utilizing normal gravitational forces to promote separation of the extractor layers, centrifugal separations may be employed, and extraction conditions may be changed. Similarly, various combinations of temperature and pressure may be utilized to promote vaporization, evaporation and stripping. Different desired final concentrations of materials are also obtainable by procedural changes in the described method. Yet, despite all such variations in the method, and despite deoilings of various detergents, the method and apparatus operate efficiently, allowing the purification of the detergents without unacceptable losses of product, in a closed system from which solvents employed do not escape to cause air pollution and other problems, and in which system the various solvents are reused continuously. The method may be employed for removing free oil from aqueous detergent solutions containing larger proportions of inorganic salt and is also useful for the purification of detergents that are essentially free of such salts. Of course, if too much inorganic salt, e.g., sodium sulfate, is present in the aqueous detergent solution being purified of free oil it may be thrown out of solution when it is brought into contact with the isopropanol in the mixer and in the extracting medium. This could be bothersome in subsequent operations and could result in a product of too high a salt content. Therefore, it may be desirable, when such an excess of inorganic salt is present, to separate at least some of it out initially, as by isopropanol treatment and filtration or settling, before carrying out the extracting, vaporizing, evaporating and stripping steps of this invention.

In another modification of the process of this invention, the portion of extracted material from the lower part of the extractor may be fed directly to the stripper, rather than to an intervening evaporator, although the use of the evaporator is highly preferred. In such operation, the stripper overhead may be recycled back to the mixer, to which the evaporator overhead would otherwise have been sent, or a portion of the stripper overhead, e.g., 25 to 75%, may be sent to the neutralizer, with the remainder thereof being sent to the mixer. In other variations of the invention recyclings of removed materials, including lipophilic and hydrophilic solvents, may be modified. For example, when employing the evaporator the stripper overhead may be recycled at least in part to the mixer or other suitable apparatus prior to stripping, instead of all of it being sent to the neutralizer.

The stripper apparatus described may be utilized for other stripping operations involving detergent solutions or may be employed for stripping of materials other than detergents, being especially useful when the materials tend to foam during distillation, rectification, stripping and similar processing operations. The stripping apparatus of this invention is also useful for stripping volatilizable materials from non-foaming compositions because it allows high speed movement of the stripping gas and vapor, e.g., steam plus volatilized solvent, through the stripper without objectionable entrainment, which is otherwise often encountered. In other words, the foam breaking means of the present stripping apparatus and the flow patterns in the apparatus, while exceedingly useful for preventing objectionable foaming and foam entrainment in the stripping gas, is also useful for preventing undesirable non-foam droplet or other entrainment of material in the stripping medium. For example, the present stripper may be employed for stripping volatiles from petroleum oils and use of the stripper allows higher throughputs than are obtainable with conventional bubble tray units.

The invention has been described with respect to various embodiments, including two illustrations and an example of different aspects thereof, but is not to be limited to these because it is evident that one of skill in the art, with the present teaching before him, will be able to utilize substitutes and equivalents without departing from the invention.

What is claimed is:

1. A method for deoiling a water-soluble salt of a $C_{10}$–$C_{18}$ alkyl sulfate detergent in an aqueous medium containing oil therein which comprises the steps of admixing an aqueous detergent containing 25% to 33% by weight of said sulfate detergent and 1% to 6% of oil to be removed with a mixture of $C_1$–$C_3$ aliphatic alcohol, $C_4$–$C_9$ hydrocarbon and water to form a single-phase liquid containing said detergent, said oil, water, $C_1$–$C_3$ aliphatic alcohol and $C_4$–$C_9$ hydrocarbon in which the weight ratio of aliphatic alcohol to said detergent is within the range of 1.3:1 to 2.5:1 by weight; contacting said single-phase liquid detergent solution from the preceding step with an extractant solution containing liqiud $C_1$–$C_3$ aliphatic alcohol and a liquid $C_4$–$C_9$ hydrocarbon, said extractant solution being in substantial equilibrium with said liquid detergent solution except for the oil content thereof so as to extract oil from said single-phase detergent liquid without significantly altering the balance of the composition of said detergent solution; separating such liquids into two portions substantially corresponding to those before contacting is effected, with $C_4$–$C_9$ hydrocarbon, $C_1$–$C_3$ alcohol and free oil in the first portion and alkyl sulfate, $C_1$–$C_3$ alcohol, water and $C_4$–$C_9$ hydrocarbon in the second portion; separating the $C_4$–$C_9$ hydrocarbon and $C_1$–$C_3$ alcohol from the free oil of said first portion; evaporating said second portion material to remove portions of $C_1$–$C_3$ alcohol, $C_4$–$C_9$ hydrocarbon and water therefrom and to increase the concentration of said alkyl sulfate salt in the aqueous solution thereof; stripping $C_1$–$C_3$ alcohol from the concentrated alkyl sulfate solution resulting; returning the $C_4$–$C_9$ hydrocarbon and $C_1$–$C_3$ alcohol after removal of free oil therefrom back to the extraction step; adding the $C_1$–$C_3$ alcohol, $C_4$–$C_9$ hydrocarbon and water mixture removed from the extracted detergent solution back to said aqueous detergent solution prior to extraction thereof; and recycling the $C_1$–$C_3$ alcohol stripped off the detergent solution to another step of this method.

2. A method of deoiling a water-soluble salt of a sulfonated or sulfated anionic detergent having an alkyl group of 8 to 20 carbon atoms in its molecular structure in an aqueous medium containing oil therein which comprises the steps of admixing an aqueous detergent containing 25% to 33% by weight of said detergent and 1% to 6% of oil to be removed with a mixture of $C_1$–$C_3$ aliphatic alcohol, $C_4$–$C_9$ hydrocarbon and water to form a single-phase liquid containing said detergent, said oil, water, $C_1$–$C_3$ aliphatic alcohol and $C_4$–$C_9$ hydrocarbon in which the weight ratio of aliphatic alcohol to said detergent is within the range of 1.3:1 to 2.5:1 by weight, contacting said single-phase liquid detergent solution from the preceding step with an extractant solution containing liquid $C_1$–$C_3$ aliphatic alcohol and a liquid $C_4$–$C_9$ hydrocarbon, said extractant solution being in substantial equilibrium with said detergent solution except for the oil content thereof so as to extract oil from said single-phase detergent liquid without significantly altering the balance of the composition of said detergent solution; separating such liquids into two portions substantially corresponding to those before contacting is effected, with $C_4$–$C_9$ hydrocarbon, $C_1$–$C_3$ alcohol and free oil in the first portion and anionic salt, $C_1$–$C_3$ alcohol, water and $C_4$–$C_9$ hydrocarbon in the second portion; separating the $C_4$–$C_9$ hydrocarbon and $C_1$–$C_3$ alcohol from the free oil of said first portion; and recycling said recovered mixture of $C_1$–$C_3$ alcohol and $C_4$–$C_9$ hydrocarbon to said extraction step for use in extracting oil from additional aqueous anionic detergent salt.

3. A method according to claim 1 wherein the first and second portions are upper and lower body portions, respectively, in an extractor.

4. A method according to claim 3 wherein the composition of the detergent solution for extraction is adjusted in a mixer before the extractor by mixing neutralized base, comprising said alkyl sulfate, free oil, water and $C_1$–$C_3$ alcohol, with a mixture of $C_1$–$C_3$ alcohol, $C_4$–$C_9$ hydrocarbon and water recovered from evaporation of the second portion from the extraction step.

5. A method according to claim 4 wherein the temperature of the mixture in the extractor is in the range of 15° to 70° C.

6. A method according to claim 5 wherein said alkyl sulfate is sodium lauryl sulfate, said $C_1$–$C_3$ alcohol is isopropanol, said $C_4$–$C_9$ hydrocarbon is hexane, the temperature of the mixture in the extractor is in the range of 30° to 35° C., and the hexane and isopropanol are distilled off from the free oil at a temperature in the range of 65° to 90° C. and at a pressure of 0.9 to 1.1 atmosphere.

7. A method according to claim 6 wherein the concentration of sodium lauryl sulfate in the evaporator product is 27 to 37% by weight, isopropanol, hexane and water, removed from the evaporator separate from the evaporated product, are mixed with the aqueous solution of sodium lauryl sulfate before extraction of free oil therefrom, to produce a solution that is immiscible with and in equilibrium with the extractant, and the concentration of sodium lauryl sulfate in the stripper product is 25 to 35% by weight.

8. A method according to claim 7 wherein the temperatures and pressures in the evaporator and stripper are within the range of 25° to 100° C. and 150 to 350 torr.

9. A method according to claim 8 wherein the aqueous solution of sodium lauryl sulfate being deoiled contains from 3.2 to 19.4 parts of free oil per hundred parts of sodium lauryl sulfate and from 1 to 9.7 parts of sodium sulfate per hundred parts of sodium lauryl sulfate.

10. A method according to claim 9 wherein the sodium lauryl sulfate being deoiled is that resulting from sulfur trioxide sulfation of lauryl alcohol and neutralization by sodium hydroxide of the sulfuric reaction product made, and the free oil being removed from the sodium lauryl sulfate is that resulting from such reactions.

11. A method according to claim 10 wherein evaporation of the lower body portion material from the extractor is effected in a wiped-film evaporator.

12. A method according to claim 1 wherein the concentrated alkyl sulfate solution is countercurrently steam stripped in a stripping column having a plurality of contacting zones therein, with steam being admitted to said column near one end thereof, mixed consecutively with different portions of aqueous solution of product to be stripped, consecutively separated from such portions of liquid, and passed out near the other end of the column, enriched in isopropanol, and with such solution being stripped passing through the column in an opposite direction, to be consecutively contacted by such steam or vapor of lower isopropanol content.

13. A method according to claim 11 wherein the liquid lauryl sulfate evaporator product is countercurrently steam stripped in a stripping column having a plurality of contacting zones therein, with steam being admitted to said column near one end thereof, mixed consecutively with different portions of aqueous solution of product to be stripped, consecutively separated from such portions of liquid, and passed out near the other end of the column, enriched in isopropanol, and with such solution being stripped passing through the column in an opposite direction, to be consecutively contacted by such steam or vapor of lower isopropanol content.

14. A method according to claim 1, which is continuous.

15. A method according to claim 13 wherein the steam and water-isopropanol vapor generated by it move upwardly through the column and detergent solution to be stripped moves downwardly through it, with the flow of the steam or the water-isopropanol vapor repeatedly drawing into contact with it liquid to be stripped and with such liquid-vapor mixtures made being repeatedly separated into liquid and vapor streams.

16. A method according to claim 2 wherein the aqueous medium containing anionic salt and oil therein is one which intially is not in equilibrium with the extractant solvent and which is converted to a solution in equilibrium therewith by addition to it of such $C_1$–$C_3$ aliphatic alcohol and liquid $C_4$–$C_9$ hydrocarbon.

17. A method according to claim 16 wherein the synthetic detergent of the detergent solution is sodium lauryl sulfate, the lower aliphatic alcohol is isopropanol, the liquid hydrocarbon is hexane and the isopropanol and hexane added to the detergent solution to bring it into equilibrium with the extractant liquid are added as a mixture containing water.

* * * * *